United States Patent [19]

Wiley et al.

[11] 4,064,340

[45] Dec. 20, 1977

[54] NOGAMYCIN AND PROCESS OF PREPARATION

[75] Inventors: Paul F. Wiley; Jian L. Johnson, both of Kalamazoo, Mich.

[73] Assignee: The Upjohn Company, Kalamazoo, Mich.

[21] Appl. No.: 748,717

[22] Filed: Dec. 9, 1976

[51] Int. Cl.$^2$ ........................................... C07H 15/26
[52] U.S. Cl. ..................................... 536/17; 424/180; 536/4
[58] Field of Search ...................................... 536/17, 4

[56] References Cited

U.S. PATENT DOCUMENTS

| | | | |
|---|---|---|---|
| 3,183,157 | 5/1965 | Bhuyan et al. | 424/120 |
| 3,501,569 | 3/1970 | Wiley et al. | 424/119 |
| 3,976,667 | 8/1976 | Kelly | 536/17 |

OTHER PUBLICATIONS

Noller "Chem. of Organic Cpds.", 3rd Ed. 1965, W. B. Saunders Co., Philadelphia, Pa., pp. 597 and 678.

Primary Examiner—Johnnie R. Brown
Attorney, Agent, or Firm—Roman Saliwanchik

[57] ABSTRACT

Novel antibiotic, nogamycin (U-51,204) prepared chemically from nogalamycinic acid. Nogamycin is active against various microorganisms, for example, *Mycobacterium avium, Bacillus subtilis, Lactobacillus casei, Staphylococcus aureus,* and *Sarcina lutea.* Thus, nogamycin can be used to inhibit the growth of the above microorganisms in various environments.

4 Claims, No Drawings

NOGAMYCIN AND PROCESS OF PREPARATION

The invention described herein was made in the course of, or under Contract NO1-CM-43753 with the National Cancer Insititutes of Health, Bethesda, Md. 20014.

BACKGROUND OF THE INVENTION

The known antibiotic nogalamycin, and a process for its preparation, are described in U.S. Pat. No. 3,183,157. The structure of nogalamycin can be shown as follows:

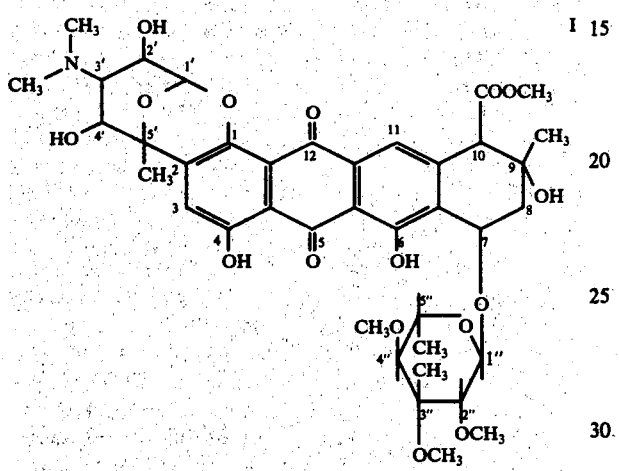

Antibiotics nogalarol and nogalarene, produced by acid hydrolysis of nogalamycin, and o-methylnogalarol, produced by acidic methanolysis of nogalamycin or nogalarol, are disclosed in U.S. Pat. No. 3,501,569.

Nogalamycinic acid is prepared by chemical modification of nogalamycin. The structure of nogalamycinic acid is as follows:

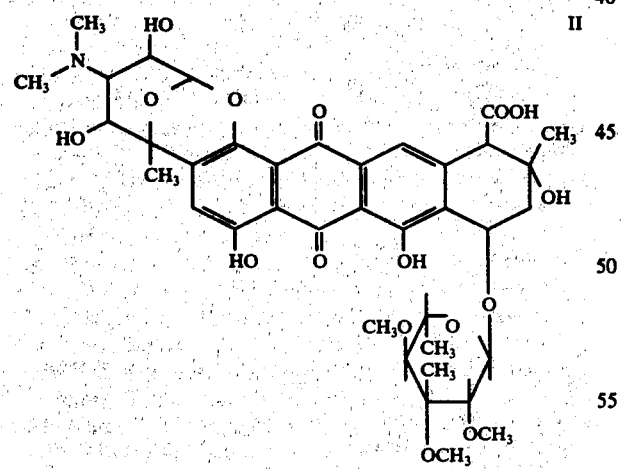

BRIEF SUMMARY OF THE INVENTION

Nogamycin can be prepared chemically from nogalamycinic acid. The reaction comprises contacting nogalamycinic acid with dimethylformamide (DMF). Alternatively, nogalamycinic acid can be converted to nogamycin by contacting it with dimethylacetamide (DMA) or dimethylsulfoxide (DMSO). Nogamycin is biologically active, as disclosed above, and can be used in various environments to inhibit the growth of suscep-tible microorganisms. For example, nogamycin can be used for treating breeding places of silkworms, to prevent or minimize infections which are well known to be caused by *Bacillus subtilis*. Further, nogamycin can be used to control *Mycobacterium avium* which is a known producer of generalized tuberculosis in birds and rabbits.

DETAILED DESCRIPTION OF THE INVENTION

Nogamycin can be shown by the following structure:

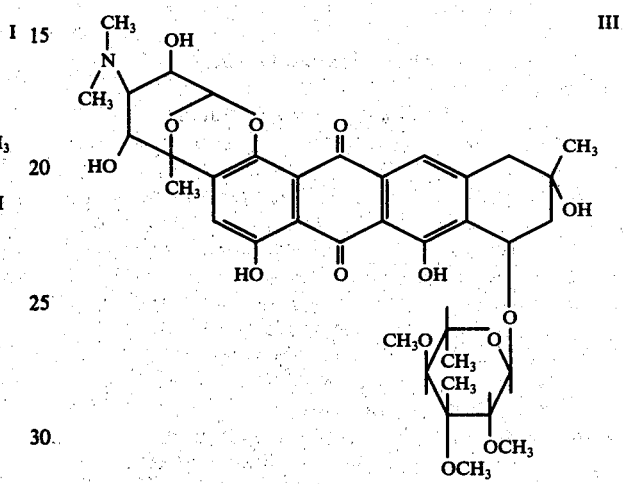

Nogamycin can be prepared by contacting nogalamycinic acid with DMF at a temperature of about 20°–80° C. Suitable substitutes for DMF are DMA and DMSO.

Nogamycin can be acylated under standard acylating conditions with an appropriate acid halide or anhydride to give the acylated compounds. The acylation is carried out in the presence of an acid-binding agent. Suitable acid-binding agents include: amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like, (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, notro-, amino-, cyano-, and lower alkoxy- hydrocarbon carboxylic acids include hydrocarboncarboxlic acids as given above which are substituted by one or more of halogen, nitro, amino, cyano, or lower alkoxy, advantageously lower alkoxy of not more than six carbon atoms, for example, methoxy, ethoxy, propoxy, butoxy, amyloxy, hexyloxy groups and isomeric forms thereof. Examples of such substituted hydrocarbon carboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
cyanopropionic acid;
ethoxyformic acid (ethyl hydrogen carbonate);

and the like.

The acylated compound, as described above, can be used in animals for the same biological purposes as disclosed above for nogamycin. For example, the acylated compounds can be given in oral form to an animal possessing the necessary enzyme to remove the acyl group, thus freeing the parent antibiotic compound which then inhibits susceptible bacteria.

Acid addition salts of nogamycin can be made by neutralizing nogamycin with an appropriate acid to below about pH 7.0, and advantageously to about pH 2 to pH 6. Suitable acids for this purpose include tartaric, glucuronic, and lactic which give water soluble salts, and hydrocholoric, sulfuric, phosphoric, sulfamic, hydrobromic, and the like which give relatively water insoluble salts. Acid salts of nogamycin can be used for the same biological purposes as the parent compound.

Nogamycin has demonstrated antitumor activity against L1210 in vitro, and against P388 in vivo in mice.

The following examples are illustrative of the process and products of the invention, but are not to be construed as limiting. All percentages are by weight and all solvent mixture proportions are by volume unless otherwise noted.

Preparation of Nogalamycinic Acid

Forty grams (0.05 mole) of nogalamycin was dissolved in 356 ml of 1 N KOH (0.36 mole), and 310 ml of water was added. The solution was stirred overnight at room temperature. The reaction mixture was acidified to pH 3.0 by adding 30% $H_2SO_4$ dropwise with stirring. The precipitate was collected by centrifugation and the precipitate was washed three times with water. The dried product weighted 28.5 g. Ten grams was dissolved in 125 ml of methanol and put on 500 g of silica packed in $CHCl_3$—MeOH (95:5). Developed with $CHCl_3$—MeOH (95:5) increasing gradually to $CHCl_3$—MeOH (4:1). Elution was continued with $CHCl_3$—MeOH (1:1) until nogalamycinic acid had been eluted as determined by thin layer chromatography (tlc) using $CHCl_3$—MeOH—$H_2O$ (78:20:2). Evaporation in vacuo of the fractions containing chromatographically pure material gave a red solid, wt. 2.3 g; mp 219°–229° C.; Rf (tlc, $CHCl_3$—MeOH—$H_2O$; 78:20:2) 0.25; $a_D$ +456° (C 0.37, $CH_3OH$); uv (EtOH) λmax nm 236 (ε 39,950), 269 (ε 21,350), 291 sh (ε 8,700), 482 (13,550); ir (Nujol) 3450, 1670, 1630, 1595, 1580, 1290, 1230, 1215, 1135, 1095, 1060, 1015, 980, 920, 855, 830, 780, 763 and 725 cm$^{-1}$; mass spectrum m/e 729 (M$^-$ —$CO_2$); $^1$H NMR ($CDCl_3$—$CD_3OD$) δ 1.38 (m, 9 H, 3 $CH_3C$), δ 1.80 (s, 3 H, $CH_3C$), δ 3.15 (s, 6H, $(CH_3)_2NH^+$), δ 3.38, 3.40, 3.68 (3 s, 9 H, 3 $CH_3O$), δ 3.2–4.0 (m, CHO and CHN), δ 5.24 (d, 1 H, anomeric), δ 5.88 (d, 1 H, anomeric), δ 6.92 (s, 1 H, aromatic) and δ 7.47 (s, 1 H, aromatic); $^{13}$C NMR ($CDCl_3$—$CD_2OD$) 16.4, 19.3, 24.6, 31.5 (4 $CH_3C$), δ 42.5 [$(CH_3)_2N$], δ 49.9, 58.2, 60.3, 62.5, 67.8, 68.5, 70.6, 71.6, 74.0, 77.3, 79.6, 82.1 and 85.9 ($CH_3O$, CHO and CHN), δ 97.3 and 100.2 (anomeric), δ 113.1, 114.1, 116.0, 120.7, 125.8, 131.0, 132.5, 137.2, 147.4, 147.8, 156.0 and 161.4 (aromatic), δ 178.9, 181.9, 181.6 and 191.4 (carbonyl).

EXAMPLE 1

Nogamycin

A solution of 12.3 g of nogalamycinic acid in a mixture of 20 ml of DMF and 50 ml of $CH_3OH$ was prepared by heating. After the solution had stood at room temperature overnight, it was put on 500 g of silica and eluted with $CHCl_3$—MeOH starting with 99:1 and gradually increasing the concentration of $CH_3OH$ until a ratio of 4:1 was reached. The elution was followed by thin layer chromatography (tlc) ($CHCl_3$—MeOH—$H_2O$; 78:20:2) and collecting those fractions containing only nogamycin (Rf 0.5). A total of 3.9 g was obtained. One and one-half grams was recrystallized from acetone-$CH_3OH$ (85:15). Obtained: 259 mg, mp 210°–215° C.; $a_D$ +273° (C 0.923, $CHCl_3$); uv (EtOH) λmax nm 236 (ε 51,700), 259 (ε 25,850), 290 (ε 10,050) and 478 (ε 16,100); ir (Nujol) 3500, 1670, 1630, 1575, 1295, 1230, 1110, 1055, 1005, 920, 890, 838, 778, 762 and 724 cm$^{-1}$; mass spectrum m/e 729; $^1$H NMR ($d_7$-DMF) 1.14, 1.23, 1.37, 1.69 (12 H, 4 $CH_3C$), δ 2.07–2.38, 2.83–3.0 (m, 4 H, 2 $CH_2$), 2.42 [s, 6 H, $(CH_3)_2N$], δ 3.13, 3.42, 3.52 (3 S, 9 H, 3 $CH_3O$), 3.3–4.2 (m, CHO, CHN), 4.95 (m, 1 H, benzylic CHO), δ 5.32 (d, 1 H, anomeric), δ 5.68 (1 H, anomeric) δ 7.16, 7.32 (2s, 2 H, aromatic); $^{13}$C NMR ($CDCl_3$) δ 15.2, 18.3, 24.2, 30.4 (4 $CH_3C$), 30.8 ($CH_2$), δ 41.5 [$(CH_3)_2N$], δ 44.1 ($CH_2$) δ 48.7, 59.0, 61.4 (3 $CH_3O$), δ 66.4–88.6 (CO and CN), δ 96.79 and 99.81 (anomeric), δ 113.1–161.4 (aromatic), δ 179.7 and 190.8 (carbonyl).

Anal. calcd. for $C_{37}H_{47}NO_{14}$: C, 60.96; H, 6.55; N, 1.92. Found: C, 58.55; H, 6.42; N, 1.94.

| Antimicrobial Activity Of Nogamycin | |
|---|---|
| Organism | Zone Size (mm) |
| *Sacharomyces pastorianus* | 0 |
| *Mycobacterium avium* | 24 |
| *Klebsiella pneumoniae* | 0 |
| *Bacillus subtilis* | 28 |
| *Lactobacillus casei* | 38 |
| *Staphylococcus aureus* | 19 |
| *Proteus vulgaris* | 0 |
| *Escherichia coli* | 0 |
| *Salmonella schottmuelleri* | 0 |
| *Sarcina lutea* | 28 |
| *Penicillium oxalicum* | 0 |

The above antimicrobial tests were run by dipping 13 mm filter paper discs into a 1 mg/ml solution of the test substance in methanol (uptake about 20 microliters/-disc) and placing the discs on agar plates containing a 1.3 mm layer of agar freshly seeded with the test organism. Discs dipped in methanol alone gave no inhibition zones. The agar media used, available from the Difco Company, Detroit, Michigan, were as follows: for *B. subtilis* and *K. pneumoniae*, Streptomycin agar; for *S. lutea*, Penassay agar; for *L. casei*, thioglycollate agar; for *S. aureus, P. vulgaris, E. coli, S. schottmuelleri*, nutrient agar; for *M. avium*, Brain Heart Infusion agar; for *P. oxalicum*, malt extract agar; and, for *S. pastorianus*, Gray's medium which has the following ingredients:

| | Gm/liter $H_2O$ |
|---|---|
| Glucose | 30 |
| Yeast Extract | 7 |
| $KH_2PO_4$ | 5 |
| Agar | 15 |

The plates were incubated 18 to 24 hours at 37° C., except for those containing *S. lutea* which were incubated at 32° C., before reading the zones.

We claim:

1. Nogamycin, a compound having the following structure:

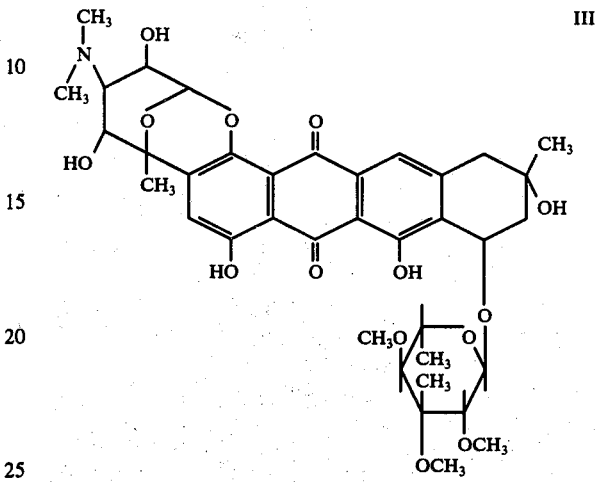

2. Acylates of nogamycin wherein said acyl group consists of hydrocarbon carboxylic acid acyl of from 2 to 18 carbon atoms, inclusive; halo-, nitro-, amino-, cyano-, and lower alkoxy-substituted hydrocarbon carboxylic acid acyl of from 2 to 18 carbon atoms, inclusive.

3. A process for preparing nogamycin which comprises contacting nogalamycinic acid with dimethylformamide at a temperature of about 20° C. to about 80° C.

4. Biologically acceptable acid addition salts of nogamycin.

* * * * *

UNITED STATES PATENT OFFICE
CERTIFICATE OF CORRECTION

Patent No. 4,064,340  Dated December 20, 1977

Inventor(s) Paul F. Wiley and Jian L. Johnson

It is certified that error appears in the above-identified patent and that said Letters Patent are hereby corrected as shown below:

Column 1, line 6, for "National Cancer Institutes" read -- National Cancer Institute, National Institutes --; line 50, for "$\overset{\mid}{H}O$" read -- $\overset{\mid}{H}O$ --.

Column 3, line 3, for "hydrocarboncarboxlic" read -- hydrocarboncarboxylic --. Column 4, line 26, for "(M⁻" read -- (M⁺ --; lines 37-38, for "δ178.9, 181.9, 181.6" read -- δ178.9, 181.6 --. Column 5, line 7, for "Sacharomyces" read -- Saccharomyces --.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks